US012758340B2

(12) United States Patent
Murugappan et al.

(10) Patent No.: US 12,758,340 B2
(45) Date of Patent: Oct. 13, 2026

(54) SYSTEMS AND METHODS FOR REMOTE MENTORING IN A ROBOT ASSISTED MEDICAL SYSTEM

(71) Applicant: INTUITIVE SURGICAL OPERATIONS, INC., Sunnyvale, CA (US)

(72) Inventors: Sundar Murugappan, Danville, CA (US); Mitchell Doughty, Mountain View, CA (US); Govinda Payyavula, Sunnyvale, CA (US); Matthew S. Warren, Ramona, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 240 days.

(21) Appl. No.: 18/835,266

(22) PCT Filed: Jan. 25, 2023

(86) PCT No.: PCT/US2023/061246

§ 371 (c)(1),
(2) Date: Aug. 1, 2024

(87) PCT Pub. No.: WO2023/150449

PCT Pub. Date: Aug. 10, 2023

(65) Prior Publication Data

US 2025/0134610 A1 May 1, 2025

Related U.S. Application Data

(60) Provisional application No. 63/305,915, filed on Feb. 2, 2022.

(51) Int. Cl.
*A61B 34/37* (2016.01)
*A61B 34/00* (2016.01)
*A61B 90/00* (2016.01)

(52) U.S. Cl.
CPC .............. *A61B 34/37* (2016.02); *A61B 34/25* (2016.02); *A61B 90/361* (2016.02); *A61B 2090/3614* (2016.02); *A61B 2090/365* (2016.02)

(58) Field of Classification Search
CPC ....... A61B 34/37; A61B 34/25; A61B 90/361; A61B 2090/3614; A61B 2090/365;
(Continued)

(56) References Cited

FOREIGN PATENT DOCUMENTS

| | | | |
|---|---|---|---|
| WO | WO-2016077531 | A1 | 5/2016 |
| WO | WO-2017031132 | A1 | 2/2017 |
| WO | WO-2021202609 | A1 | 10/2021 |

OTHER PUBLICATIONS

Bailey S., et al., "Remote Solution for Immersive Surgical Mentoring," Medical Education, Apr. 2020, pp. 485-486.

(Continued)

*Primary Examiner* — Rex R Holmes

(74) *Attorney, Agent, or Firm* — Haynes & Boone LLP.

(57) ABSTRACT

A non-transitory machine-readable media may store instructions that, when run by one or more processors, cause the one or more processors to generate stereo endoscopic image data of a medical field and define a medical field volume from the stereo endoscopic image data. The processors may also project a 3D representation of the medical field volume to an extended-reality display device in a remote volume. The 3D representation may include a stereoscopic image and a 3D scene generated from the stereo endoscopic image data. The processors may also generate visual guidance in the remote volume to augment the stereo endoscopic image, map the visual guidance from the remote volume to the medical field volume to generate an augmented image of the medical field volume, and project the augmented image of the medical field volume to a display device viewed by an operator of instruments in the medical field.

20 Claims, 6 Drawing Sheets

(58) Field of Classification Search
CPC ........... A61B 2017/00207; A61B 2017/00216; A61B 2090/371; A61B 2090/372; A61B 2090/502; G09B 23/285
See application file for complete search history.

(56) References Cited

OTHER PUBLICATIONS

Bailey S., et al., "Validation of Live Virtual Reality for Remote Surgical Education: a Usability Evaluation in Orthopedic Surgery," May 2021, 3 Pages.
Celebi K.C., et al., "Is Virtual Reality Streaming Ready for Remote Medical Education? Measuring Latency of Stereoscopic VR for Telementoring," Proceedings of the Human Factors and Ergonomics Society Annual Meeting, Sep. 2021, vol. 65(1), pp. 757-761.
Ciccone B.A., et al., "The Next Generation of Virtual Reality: Recommendations for Accessible and Ergonomic Design," Ergonomics in Design The Quarterly of Human Factors Applications, Mar. 2021, vol. 31(2), pp. 1-4.
International Preliminary Report on Patentability for Application No. PCT/US2023/061246, mailed Aug. 15, 2024, 14 pages.
International Search Report and Written Opinion for Application No. PCT/US2023/061246, mailed Jun. 30, 2023, 21 pages.
Invitation to Pay Additional Fees and Partial International Search Report for PCT/US2023/061246, mailed May 9, 2023, 16 pages.
Proximie., "Saving Lives by Sharing the World's Best Clinical Practice," Jan. 2022, 12 Pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

SYSTEMS AND METHODS FOR REMOTE MENTORING IN A ROBOT ASSISTED MEDICAL SYSTEM

CROSS-REFERENCED APPLICATIONS

This application is the U.S. national phase of International Application No. PCT/US2023/061246, filed Jan. 25, 2023, which designated the U.S. and claims priority to and the benefit of U.S. Provisional Application No. 63/305,915, filed Feb. 2, 2022 and entitled "Systems and Methods for Remote Mentoring in a Robot Assisted Medical System," all of which are incorporated by reference herein in their entirety.

FIELD

The present disclosure is directed to systems and methods for remote mentoring in which an extended-reality user interface device is used to display endoscopic image information and generate visual guidance.

BACKGROUND

Teleoperational robotic or robot-assisted systems include manipulation assemblies that may be remotely controlled from a primary interface system. Systems and methods for training, mentoring, or advising an operator of the primary interface system may be limited if the visual information provided to the mentor does not provide full three-dimensional information and the mentor guidance may not be generated with three-dimensional accuracy. Accordingly, it would be advantageous to provide improved methods and systems for providing remote guidance where the mentor has a complete three-dimensional experience of the surgical environment and is able to provide visual guidance with three-dimensional accuracy.

SUMMARY

The embodiments of the invention are best summarized by the claims that follow the description.

Consistent with some embodiments, a non-transitory machine-readable media may store instructions that, when run by one or more processors, cause the one or more processors to generate stereo endoscopic image data of a medical field and define a medical field volume from the stereo endoscopic image data. The processors may also project a 3D representation of the medical field volume to an extended-reality display device in a remote volume. The 3D representation may include a stereoscopic image and a 3D scene generated from the stereo endoscopic image data. The processors may also generate visual guidance in the remote volume to augment the stereo endoscopic image, map the visual guidance from the remote volume to the medical field volume to generate an augmented image of the medical field volume, and project the augmented image of the medical field volume to a display device viewed by an operator of instruments in the medical field.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 6:
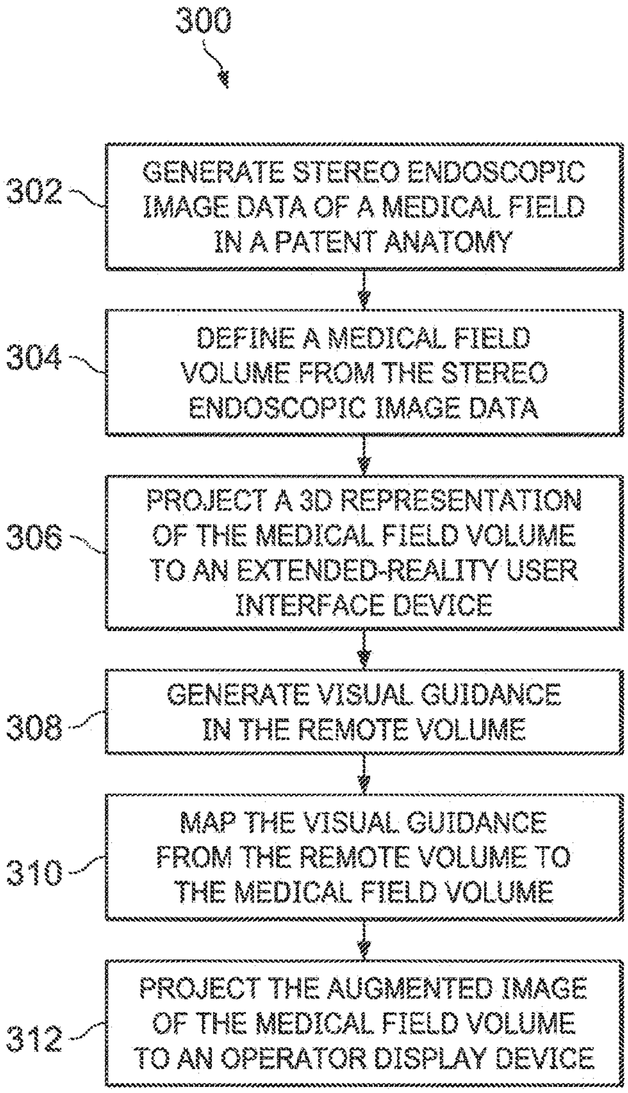

FIG. 6 is a flowchart illustrating a method for providing guidance to an operator (e.g. the surgeon S) of a primary interface system according to some embodiments Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Figure 1:
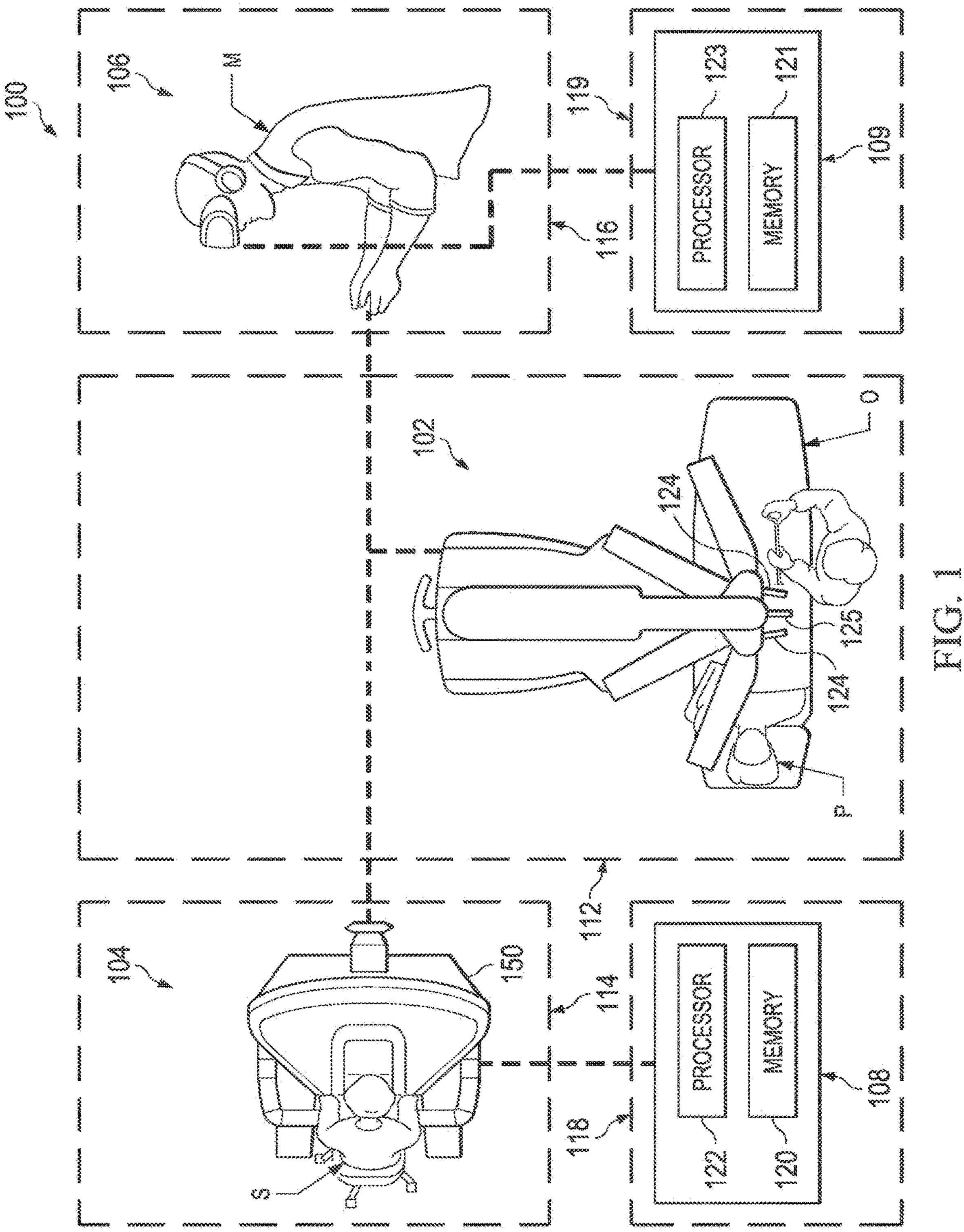
FIG. 1 is an illustration of a tele-mentoring system according to some embodiments.

FIG. 1 illustrates a tele-mentoring system 100 for mentoring, training, evaluating, assisting, guiding, advising or otherwise monitoring an operator during a teleoperational procedure, including a live patient procedure, a training procedure, a simulation procedure or other guidance procedure. The tele-mentoring medical system 100 that may be used in, for example, medical procedures including diagnostic, therapeutic, or surgical procedures. In one or more embodiments, the system 100 may be a teleoperational or robot-assisted medical system that is under the teleoperational control of a surgeon S. In alternative embodiments, the system 100 may be under the partial control of a computer programmed to perform the medical procedure or sub-procedure. In still other alternative embodiments, the system 100 may be a fully automated medical system that is under the full control of a computer programmed to perform the medical procedure or sub-procedure with the system 100. One example of the system 100 that may be used to implement the systems and techniques described in this disclosure is the da Vinci® Surgical System manufactured by Intuitive Surgical Operations, Inc. of Sunnyvale, California.

The system 100 includes a manipulator assembly 102, a primary interface system 104, a secondary interface system 106, a primary control system 108, and a secondary control system 109. The manipulator assembly 102 may be mounted to or positioned near an operating table O on which a patient P is positioned. The assembly 102 may be referred to as a patient side cart, a surgical cart, a surgical robot, a manipulating system, and/or a teleoperational arm cart.

The manipulator assembly 102 may be located in an environment 112. The primary interface system 104 may be located in an environment 114. The secondary interface system may be located in an environment 116. The primary control system 108 may be located in an environment 118. The secondary control system 109 may be located in an environment 119. In some embodiments, the environment 112 may be a medical environment such as an operating room. In other embodiments, the medical environment may be an emergency room, a medical training environment, a medical laboratory, or some other type of environment in which any number of medical procedures or medical training procedures may take place. The environment 114 may be in the environment 112, in another room in a common facility with environment 112, or in another geographic location. The environment 116 may be in the environment 112 or the environment 114, in another room in a common facility with environment 112 or 114, or in another geographic location. The environment 118 may be in the environment 112 or 114; in another room in a common facility with environment 112 or 114; or in another geographic location. The environment 119 may be in the environment 112 or 116; in another room in a common facility with environment 112 or 116; or in another geographic location. In some embodiments, the primary and secondary control systems 108, 109 may be a single control system located proximate to the primary interface system, proximate to the secondary interface system, or at a location remote from both the primary and secondary interface systems. In some embodiments, control system components used to effect communication, control, and image data transfer between the primary interface system 104, the secondary interface system 106, and the manipulator assembly 102 may be distributed over one or more locations.

Figure 2A:
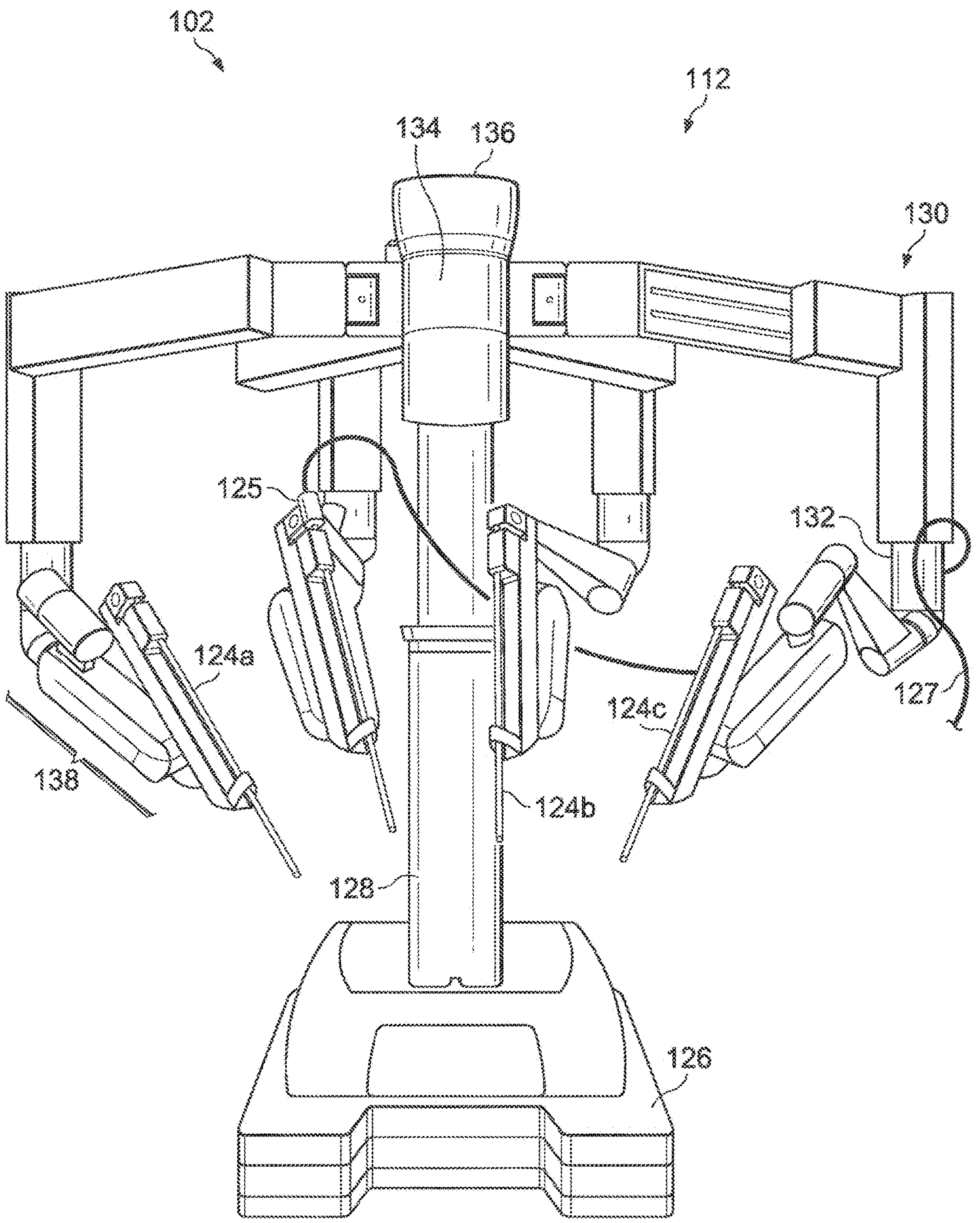
FIG. 2A is a perspective view of a teleoperational assembly according to some embodiments.

With further reference to FIG. 2A, one or more medical instrument systems 124 and an endoscopic imaging system 125 are operably coupled to the assembly 102. The medical instrument system 124 may comprise one or more medical instruments. In embodiments in which the medical instrument system 124 comprises a plurality of medical instruments, the plurality of medical instruments may include multiple of the same medical instrument and/or multiple different medical instruments. Similarly, the endoscopic imaging system 125 may comprise one or more endoscopes. In the case of a plurality of endoscopes, the plurality of endoscopes may include multiple of the same endoscope and/or multiple different endoscopes. The assembly 102 supports and manipulates the medical instrument system 124 while a surgeon S views the surgical site through the primary interface system 104. Endoscopic image data of the surgical site may be obtained by the endoscopic imaging system 125, which may be manipulated by the assembly 102. The number of medical instrument systems 124 used at one time will generally depend on the diagnostic or surgical procedure to be performed and on space constraints within the operating room, among other factors. The assembly 102 may include a kinematic structure of one or more non-servo controlled links (e.g., one or more links that may be manually positioned and locked in place, generally referred to as a manipulator support structure) and a manipulator. The assembly 102 includes a plurality of motors that drive inputs on the medical instrument system 124. In an embodiment, these motors move in response to commands from a control system (e.g., primary control system 108). The motors include drive systems which when coupled to the medical instrument system 124 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 124 may include end effectors having a single working member such as a scalpel, a blunt blade, an optical fiber, or an electrode. Other end effectors may include, for example, forceps, graspers, scissors, or clip appliers.

The assembly 102 shown provides for the manipulation of three medical instruments 124*a*, 124*b*, and 124*c* and an endoscopic imaging device 125, such as a stereoscopic endoscope used for the capture of images of the site of the procedure. The imaging device 125 may transmit signals over a cable 127 to the primary control system 108. The imaging device 125 and the medical instrument 124*a-c* can be positioned and manipulated through incisions in the patient so that a kinematic remote center is maintained at the incision to minimize the size of the incision. Images of the surgical site can include images of the distal ends of the medical instruments 124*a-c* when they are positioned within the field-of-view of the imaging device 125. The imaging device 125 and the medical instruments 124*a-c* may each be therapeutic, diagnostic, or imaging instruments.

The assembly 102 includes a drivable base 126. The drivable base 126 is connected to a telescoping column 128, which allows for adjustment of the height of arms 130. The arms 130 may include a rotating joint 132 that both rotates and moves up and down. Each of the arms 130 may be connected to an orienting platform 134 that is capable of 360 degrees of rotation. The assembly 102 may also include a telescoping horizontal cantilever 136 for moving the orienting platform 134 in a horizontal direction.

In the present example, each of the arms 130 connects to a manipulator arm 138. The manipulator arms 138 may connect directly to a medical instrument, 124*a-c*. The manipulator arms 138 may be teleoperable. In some examples, the arms 138 connecting to the orienting platform 134 may not be teleoperable. Rather, such arms 138 may be positioned as desired before the surgeon S begins operation with the teleoperative components. Throughout a surgical procedure, medical instruments may be removed and replaced with other instruments such that instrument to arm associations may change during the procedure.

Endoscopic imaging system 125 may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image-based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle, and shaft all rigidly coupled and hermetically sealed.

Figure 2B:
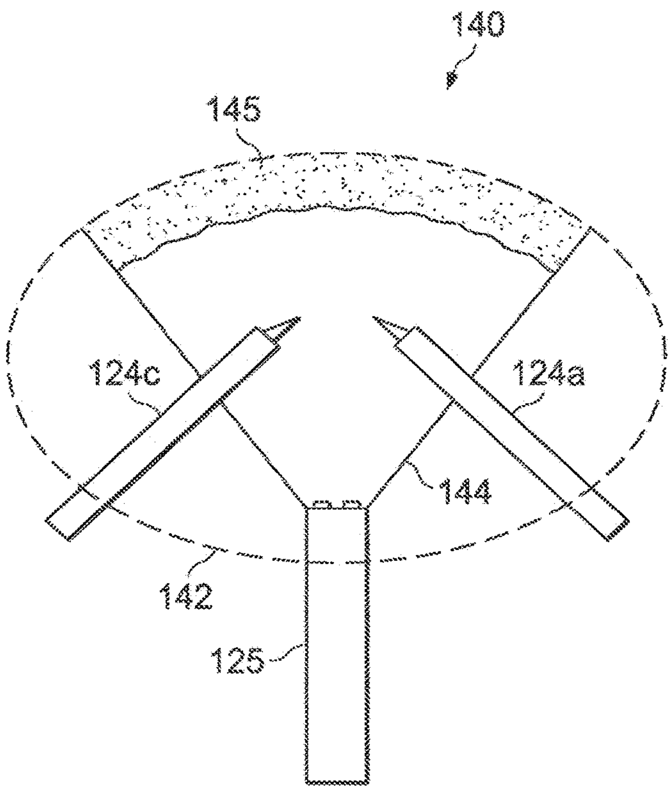
FIG. 2B illustrates a patient environment according to some embodiments.

FIG. 2B illustrates a patient environment 140 in which a distal portion of the endoscopic imaging system 125 and the distal portions of the instrument systems 124*a* and 124*c* are inserted within an anatomy 142 of the patient P. The area within the anatomy 142 visible with the imaging system 125 is an imaging field 144 that includes patient tissue 145 and the distal ends of instrument systems 124*a*, 124*c*. Interactions between the instrument system 124*a*, 124*c* and the tissue 145 in the imaging field 144 during a medical procedure may be captured by stereoscopic image data generated by the imaging system 125.

Figure 3:
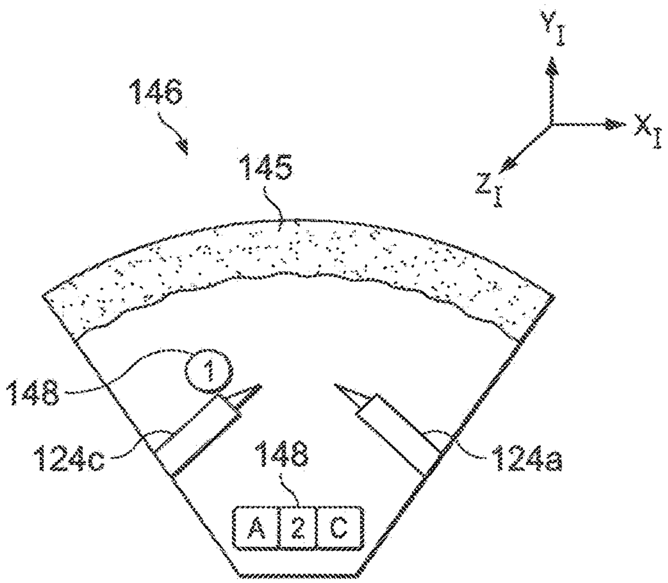
FIG. 3 illustrates a medical field volume according to some embodiments.

FIG. 3 illustrates a medical field volume 146 having a frame of reference ($X_I$, $Y_I$, $Z_I$). The medical field volume 146 may be generated from the stereoscopic image data of the imaging field 144. The medical field volume 146 may include images of the instrument systems 124*a*, 124*c* and the tissue 145 from the imaging field 144. The medical field volume 146 may also include virtual user interface elements 148 such as user interaction menus, virtual instrument marks, off-screen instrument indicators, or other graphic, numerical, and/or textual elements that provide information to a surgeon S during a medical procedure. The user interface elements 148 may be overlayed on a stereoscopic image of the medical field volume 146 or may be incorporated at selected depth positions within the medical field volume 146.

Figure 4:
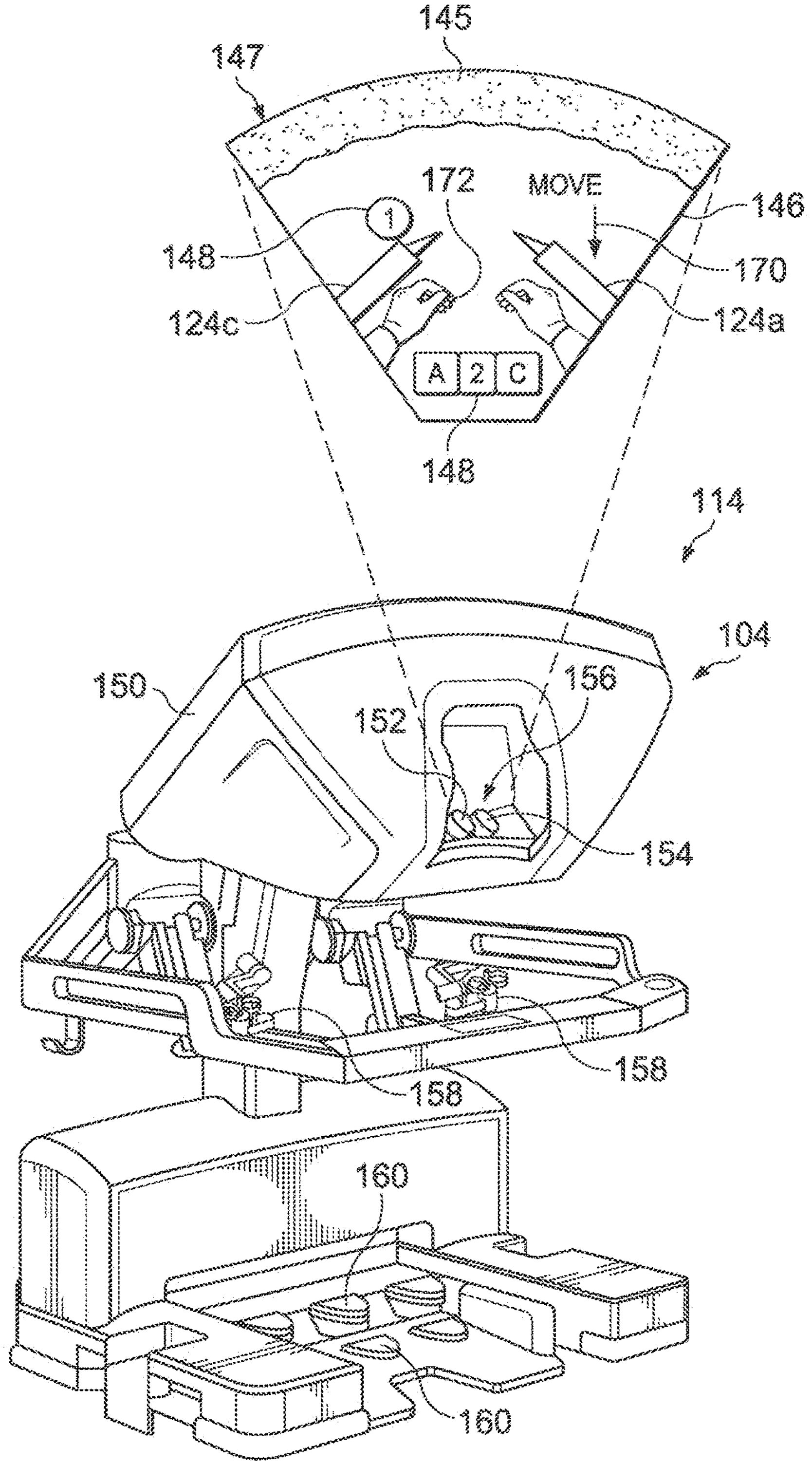
FIG. 4 illustrates a primary interface system according to some embodiments.

With reference to FIG. 4, the primary interface system 104 allows a surgeon S or other type of clinician to view images of or representing the surgical site and to control the operation of the medical instrument system 124 and/or the endoscopic imaging system 125. The primary interface system 104 may be located at a surgeon's control console 150. In one or more embodiments, the primary interface system 104 may be referred to as an operator interface system, an operator input system, a user control system, a user input system, or the like. The primary interface system 104 may include a primary display system 156 that displays image data for conducting the teleoperational procedure, including endoscopic images from within a patient anatomy, guidance information from the secondary interface system, patient information, and procedure planning information. The primary interface system 104 includes a left eye display 152 and a right eye display 154 for presenting the surgeon S with a coordinated stereo view of the surgical environment that enables depth perception. The left and right eye displays 152, 154 may be components of a display system 156. In other embodiments, the display system 156 may include one or more other types of displays. In some examples, the display system 156 may display a stereoscopic image 147 of the medical field volume 146, including the user interface elements 148. In some examples, the stereoscopic image 147 may be augmented with visual guidance 170 generated by the secondary interface system 106 as described below.

The primary interface system 104 may further include an audio system that allows the surgeon S to engage in communication with personnel in the patient environment 112 and/or personnel in the secondary interface environment 116, such as the mentor M.

The primary interface system 104 may further include one or more primary input devices 158, which in turn cause the assembly 102 to manipulate one or more instruments of the endoscopic imaging system 125 and/or the medical instrument system 124. The control device(s) may include one or more of any number of a variety of input devices, such as hand-gripped manipulation devices, joysticks, trackballs, data gloves, trigger-guns, foot pedals, hand-operated controllers, voice recognition devices, touch screens, body motion or presence sensors, and other types of input devices.

Each primary input device 158 may be movable within the environment 114 with a plurality of degrees of freedom, typically with six degrees of freedom, three rotational degrees of freedom and three translational degrees of freedom. This allows the primary input device 158 to be moved to any position and any orientation within its range of motion. The control device(s) may include one or more of any number of a variety of input devices, such as hand-gripped manipulation devices, joysticks, trackballs, data gloves, trigger-guns, foot pedals, hand-operated controllers, voice recognition devices, touch screens, body motion or presence sensors, and other types of input devices.

The kinematic range of motion and kinematic constraints associated with the medical instrument system 124, the imaging system 125, and the assembly may be provided through the primary input devices 158. The primary input devices 158 can provide the same Cartesian degrees of freedom as their associated instruments to provide the surgeon S with telepresence, or the perception that the primary input devices 158 are integral with said instruments so that the surgeon has a strong sense of directly controlling the instruments. Therefore, the degrees of freedom of each primary input device 158 are mapped to the degrees of freedom of each primary input device's 158 associated instruments (e.g., one or more of the instruments of the endoscopic imaging system 125 and/or the medical instrument system 124.). To this end, position, force, and tactile feedback sensors (not shown) may be employed to transmit position, force, and tactile sensations from the medical instruments, e.g., the medical instruments 124*a-c* or the imaging device 125, back to the surgeon's hands through the primary input devices 158. Additionally, the arrangement of the medical instruments 124*a-c* may be mapped to the arrangement of the surgeon's hands and the view from the surgeon's eyes so that the surgeon has a strong sense of directly controlling the instruments. Input control devices 160 are foot pedals that receive input from a user's foot.

Referring again to FIG. 1, the system 100 also includes the primary control system 108. The primary control system 108 includes at least one memory 120 and at least one processor 122 for effecting communication, control, and image data transfer between the medical instrument system 124, the primary interface system 104, the secondary interface system 106, and other auxiliary systems which may include, for example, imaging systems, audio systems, fluid delivery systems, display systems, illumination systems, steering control systems, irrigation systems, and/or suction systems. Though depicted as being external to the assembly 102 and primary interface 104, the primary control system 108 may, in some embodiments, be contained wholly within the assembly 102 or primary interface 104. The primary control system 108 also includes programmed instructions (e.g., stored on a non-transitory, computer-readable medium) to implement some or all of the methods described in accordance with aspects disclosed herein. While the primary control system 108 is shown as a single block in the simplified schematic of FIG. 1, the primary control system 108 may include two or more data processing circuits with one portion of the processing optionally being performed on or adjacent the assembly 102, another portion of the processing being performed at the primary interface system 104, and the like. Any of a wide variety of centralized or distributed data processing architectures may be employed in the primary control system 108. Similarly, the programmed instructions may be implemented as a number of separate programs or subroutines, or they may be integrated into a number of other aspects of the systems described herein, including teleoperational systems. In one embodiment, the control system 108 may support any of a variety of wired communication protocols or wireless communication protocols such as Bluetooth, IrDA, HomeRF, IEEE 802.11, DECT, and Wireless Telemetry.

The system 100 also includes the secondary control system 109. The secondary control system 109 includes at least one memory 121 and at least one processor 123 for effecting control between the medical instrument system 124, the secondary interface system 106, the primary interface system 104, and/or other auxiliary systems which may include, for example, imaging systems, audio systems, fluid delivery systems, display systems, illumination systems, steering control systems, irrigation systems, and/or suction systems. The secondary control system 109 may, in some embodiments, be a component of the secondary interface system 106. The secondary control system 109 also includes programmed instructions (e.g., stored on a non-transitory, computer-readable medium) to implement some or all of the methods described in accordance with aspects disclosed herein. While the secondary control system 109 is shown as a single block in the simplified schematic of FIG. 1, the secondary control system 109 may include two or more data processing circuits with one portion of the processing optionally being performed on or adjacent the assembly 102, another portion of the processing being performed at the secondary interface system 106, and the like. Any of a wide variety of centralized or distributed data processing architectures may be employed in the control system 109. Similarly, the programmed instructions may be implemented as a number of separate programs or subroutines, or they may be integrated into a number of other aspects of the systems described herein, including teleoperational systems. In one embodiment, the control system 109 may support any of a variety of wired communication protocols or wireless communication protocols such as Bluetooth, IrDA, HomeRF, IEEE 802.11, DECT, and Wireless Telemetry. In some embodiments, the primary and secondary control systems may be a single control system located proximate to the primary interface system, proximate to the secondary interface system, or at a location remote from both the primary and secondary interface systems. In some embodiments, control system components used to effect communication, control, and image data transfer between the primary interface system 104, the secondary interface system 106, and the assembly 102 may be distributed over one or more locations.

The secondary interface system 106 (also referred to as a mentor interface system) allows a mentor, proctor, instructor, advisor, or other user M at the secondary interface system 106 to receive visual and auditory information and generate guidance for the surgeon S at the primary interface system 104. The secondary interface system 106 may be operated by the mentor M to mentor, train, assist, guide, or otherwise advise the operator of the primary interface system 104 in the performance of a patient medical procedure, a simulation procedure, a training procedure or other operation performed by the surgeon S via the primary interface system 104. The secondary interface system 106 may include display system and an input system. In some examples, the interface system 106 may include an extended reality system. For example, an extended reality system may include a wearable interface device that includes a head-mounted extended-reality display device, an auditory device, and a sensor system that may track hand motions, eye gaze, head motion, speech or other mentor actions that relate to the information presented by the display device or the auditory device. In some examples, the auditory device may be integrated into the head-mounted extended-reality display device, but in other examples may be separate earphones or speakers. In some examples, the sensor system may be integrated into the head-mounted extended-reality display device, but in other examples, the sensor system may be part of a hand-held control device or an optical sensor system that uses a camera to track user motion. An extended-reality system may include a mixed-reality device, an augmented reality device, or any combination thereof that present combinations of virtual and real environments. In some examples, augmented reality devices may provide virtual information and/or virtual objects overlaid on the real world environment. In some examples, mixed-reality devices may provide virtual objects and the ability to interact with those objects within a real world environment. In some examples the mixed-reality interface device may include, for example a Microsoft Hololens or an Oculus Quest. In some examples the secondary interface system may include a three-dimensional display device in the form of a portable or desktop device.

Figure 5:
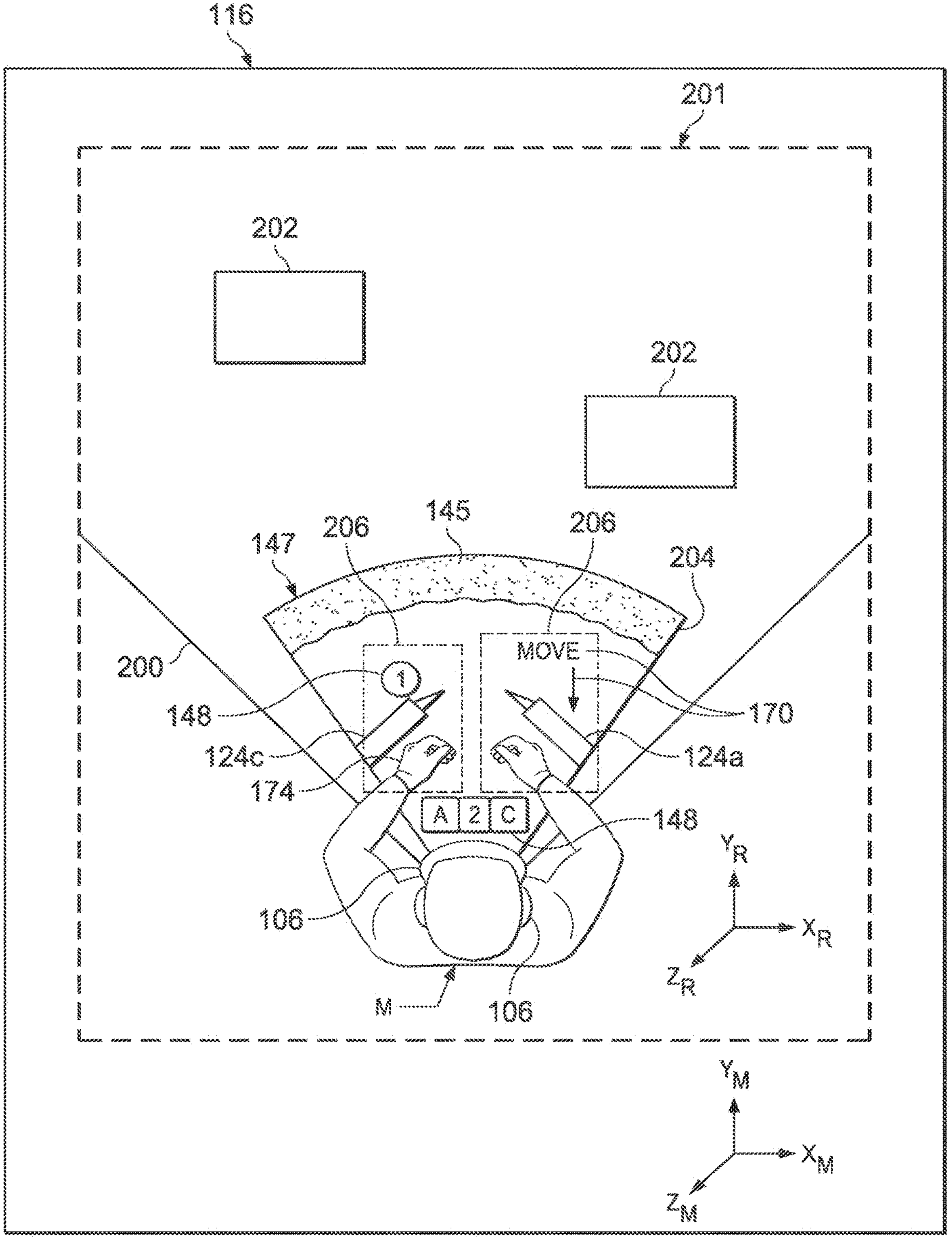
FIG. 5 illustrates an environment of a secondary interface system according to some embodiments.

With reference to FIG. 5, the mentor M may be located in the environment 116 having a frame of reference ($X_M$, $Y_M$, $Z_M$). A remote volume 201 within the environment 116 may be determined based on the mentor M's minimum, maximum, and comfort range of head movement, eye gaze, and hand reach. The remote volume 201 may have a remote frame of reference ($X_R$, $Y_R$, $Z_R$). The remote volume 201 may be egocentric to the mentor M and may physically move or rotate as the mentor moves. In some examples, the remote volume 201 may be the entire environment 116. Through the extended-reality device 106, the mentor M may view a three-dimensional representation 204 of the medical field volume 146. Through the extended-reality device 106, the mentor M may also have a field of view 200 in the remote volume 201. The field of view 200 may include objects 202 in the remote volume 201 such as furniture, other people, walls, and floor. The field of view 200 may be visible around, beyond, in front of, and through the three-dimensional representation 204 of the medical field volume.

The three-dimensional representation 204 of the medical field volume 146 may include the virtual user interface elements 148, the stereoscopic image 147 of the medical field volume 146, and one or more three-dimensional scenes 206 representing the medical field. The scene 206 may be generated, at least in part, from the stereoscopic image data of imaging field 144. Additionally or alternatively, the scene 206 may be generated from a separate depth measuring camera or other depth evaluation system. The stereoscopic image 147 may be a three-dimensional image from the viewpoint of the imaging system 125, but the three-dimensional scene 206 is three-dimensional from any viewpoint. The three-dimensional scene may be selectively constructed for discrete areas of the stereoscopic image, such as regions where the mentor's gaze intersects with the medical field volume, regions around the distal ends of instruments visible in the medical field volume, known or interesting landmarks determined based on the type of medical procedure, and/or regions where the surgeon S is viewing the medical field volume. The three-dimensional scene 206 may be generated using the imaging system intrinsic and extrinsic parameters and by determining object depths and segmenting anatomical objects. For example, object depth may be determined by matching corresponding pixels in right and left stereoscopic images based on mutual information and the approximation of a global smoothness constraint. The disparity between the matched points provides a measure of depth. Anatomical object segmentation may use graphical analysis techniques to differentiate tissue types (e.g., connective tissue and organs). The construction of three-dimensional scenes may be computationally complex, expensive, and time-consuming and so may be limited to discrete regions. In alternative examples, a three-dimensional scene with object depth determinations and anatomic segmentation may be computed for each pixel in the entire stereoscopic image 147 to generate a three-dimensional scene of the entire medical field volume 146.

The extended-reality device 106 may also be used to generate visual guidance 170 in the remote volume 201 to augment the stereoscopic image 147 of the medical field volume 146 displayed on the display system 156 of the primary interface system 104. The generated visual guidance may be mapped from the remote volume 201 to the medical field volume 146 to generate the augmented stereoscopic image 147 of the medical field volume 146 displayed on the display system 156. In some examples, the visual guidance may be located at proximate to relevant structures at a selected depth within a three-dimensional scene 206. For example, the sensor system of the extended-reality device 106 may track the mentor's free hand motions in the remote volume 201 to create visual guidance in the form of articulated ghost hand images 172 that track the motion of mentor's hands 174 at various depths within a scene 206. The user's hands may gesture, point, or provide other indications that provide guidance to the surgeon S during a medical procedure. Visual guidance in the form of the ghost hand images 172 may be placed at the tracked depths within the medical field volume 146. The visual guidance provided by the ghost hand images 172 may be visible in the stereoscopic image of the medical field volume displayed on the display system 156 of the primary interface system 104. The ghost hand images 172 may include joint positions and orientations. In some examples, more than twenty joint positions and/or orientations per hand may be used to generate the ghost hand image 172. In other examples, visual guidance may be generated by the mentor's sensed physical expressions including tracked eye gaze, head motion, body motion, speech, and/or any combination of sensor or input channels. In some examples, the tracked sensor information or other input may be used to generate visual guidance 170 in the form of arrows, pointers, ghost tools, gaze markers, and textual, numerical, or graphical annotations. In some examples, three-dimensional telestrations may be generated based on motion mapped from the palm of the mentor's hand. Hand gestures may be used to initiate and terminate generation of telestrations. In some examples the visual guidance 170, 172 may be visible in three-dimensional representation 204 of the medical field volume 146 visible to the mentor M so that the mentor may view the generated visual guidance, providing a closed-loop feedback to the mentor. The visual guidance 170, 172 may be mapped in the remote volume 201 with corresponding three-dimensional parameters such as depth, position, orientation, and velocity in the medical field volume 146. The mapping may include scaling the parameters to generate the visual guidance. The mapping may be adaptively changed as the endoscope 125 is moved or the mentor moves.

In some examples, the visual guidance may have a spatial-temporal nature which affects its behavior or display longevity. For example, an arrow placed by the mentor M (e.g., an arrow generated in the direction from the palm of the mentor's hand toward the mentor's fingertips) may disappear when the surgeon S moves the endoscope 125 because the guidance provided by the arrow may not be applicable with the changed view of the endoscope. In some examples, if an arrow is tagged to an anatomical landmark or instrument in the imaging field 144, the arrow may persist even if the surgeon moves the endoscope 125. The arrow may be deleted by affirmative action of the surgeon S. In some examples, the visual guidance may be generated only when the mentor's attention is on certain areas or types of real or virtual objects in the three-dimensional representation 204 of the medical field volume 146. In some examples, guidance is generated only when the mentor's attention (e.g., gaze intersects the scene 206) is on a three-dimensional scene 206. If the mentor's attention is elsewhere, and the mentor moves his hands, no guidance may be generated and hence the surgeon S will not sec a representation of the motion. This may prevent unintentional guidance generation. In some examples, guidance may be in the form of a virtual three-dimensional anatomical model that may be manipulated by the mentor in the three-dimensional representation 204 of the medical field volume 146. The surgeon S may view the manipulated model on the display 156. In some examples, the mentor M may manipulate user interface elements 148 to demonstrate various techniques, menu selections, or other virtual object manipulations. In some examples, the mentor M may be prevented from taking control of the instruments 124*a*, 124*c* from the remote environment 116, but in other examples, the mentor may control the instruments in the patient environment 112 from the remote environment 116. In some examples, the mentor M in the remote environment 116 may also or alternatively generate audio or haptic guidance that may be presented to the surgeon S in the surgeon environment 114.

In some examples, a real-time model of the manipulator assembly 102 may be projected to the extended-reality device 106 to be viewed alone or in context with the three-dimensional representation 204 of the medical field volume 146. The model manipulator assembly may be generated based on measured kinematic pose data, sensor data, tracked light emitting devices, detected arrows, or the like. In some examples, the model manipulator assembly may be generated based on camera images from the environment 112. By viewing the model of the manipulator assembly, the mentor M may be able to view manipulator arm collisions, warning indicators on the manipulator assembly, or other information about the manipulator assembly that may inform the mentor's understanding of the conditions in the environment 112. In some examples, the model of the manipulator assembly may be fused with the augmented medical field volume 146 and displayed on the extended-reality device 106 so that the mentor M may see the instruments extending out of the patient and coupled to the manipulator assembly.

In some examples, a real-time model of the operator console 104 may be projected to the extended-reality device 106. The model operator console may be generated based on measured kinematic pose data, sensor data, tracked light emitting devices, detected arrows, or the like. In some examples, the model operator console may be generated based on camera images from the environment 114. By viewing the model of the operator console, the mentor M may be able to view input device positions, orientations, collisions, or other information about the operator console that may inform the mentor's understanding of the conditions in the environment 114.

In some examples, the medical field volume may be a mosaic generated from multiple images taken in the patient anatomy, and the mentor M may generate the visual guidance in an area of the mosaic that is outside the view of the medical field volume currently being viewed by the surgeon S. The surgeon S may access the visual guidance by moving the imaging instrument 125 to view the area of the medical field volume in which the visual guidance has been placed.

FIG. 6 is a flowchart illustrating a method 300 for providing guidance to an operator (e.g. the surgeon S) of a primary interface system according to some embodiments.

The methods described herein are illustrated as a set of operations or processes and are described with continuing reference to the preceding figures. Not all of the illustrated processes may be performed in all embodiments of the methods. Additionally, one or more processes that are not expressly illustrated in may be included before, after, in between, or as part of the illustrated processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by any of the control systems 108, 109.

The method 300 may be performed using a tele-mentoring system (e.g., tele-mentoring system 100) allowing the mentor M at a secondary interface system (e.g., secondary interface system 14, 106) to provide visual guidance to the operator of the primary interface system. At a process 302, stereo endoscopic image data of a medical field in a patient anatomy may be generated. For example, stereoscopic image data may be generated by the imaging system 125 of the imaging field 144 in the anatomy 142.

At a process, 304, a medical field volume may be defined from the stereoscopic image data. For examples, the medical field may be generated from the stereoscopic image data of the imaging field 144. The medical field volume 146 may include images of the instrument systems 124*a*, 124*c* and the tissue 145 from the imaging field 144. The medical field volume 146 may also include virtual user interface elements 148 such as user interaction menus, virtual instrument marks, off-screen instrument indicators, or other graphic, numerical, and/or textual elements that provide information to a surgeon S during a medical procedure.

At a process 306, a three-dimensional representation of the medical field volume may be projected to an extended-reality user interface device. The three dimensional representation may include a stereoscopic image generated from the stereo endoscopic image data and a three dimensional scene generated from the stereo endoscopic image data. For example, the three-dimensional representation 204 of the medical field volume 146 may be projected to the extended-reality device 106 in the remote volume 201, allowing the mentor M to view the imaging field 144 and any virtual interface element 148. The three-dimensional representation 204 of the medical field volume 146 may include the virtual user interface elements 148, the stereoscopic image 147 of the medical field volume 146, and one or more three-dimensional scenes 206 that represent the medical field. In some examples, the mentor M may also view the field of view 200 in the remote volume 201 through the extended-reality device 106. The field of view 200 may include objects 202 in the remote volume 201 such as furniture, other people, walls, and floor. The field of view 200 may be visible around, beyond, in front of, and through the three-dimensional representation 204 of the medical field volume. In some examples, the mentor may be unable to view the field of view 200 in the remote volume 201 through the extended-reality device 106.

At a process 308, visual guidance may be generated in the remote volume. For example, the extended-reality device 106 may also be used to generate visual guidance 170 in the remote volume 201 to augment the stereoscopic image 147 of the medical field volume 146 displayed on the display system 156 of the primary interface system 104.

At a process 310, the visual guidance may be mapped from the remote volume to the medical field volume. For example, the generated visual guidance 170, 172 may be mapped from the remote volume 201 to the medical field volume 146. The extended-reality device 106 may track the mentor's free hand motions, eye gaze, head motion, body motion, speech, and/or any combination of sensor or input channels in the remote volume 201 to create visual guidance in the form of articulated ghost hand images, arrows, pointers, ghost tools, gaze markers, and textual, numerical, or graphical annotations. In some examples the visual guidance 170, 172 may be visible in three-dimensional representation 204 of the medical field volume 146 visible to the mentor M so that the mentor may view the generated visual guidance, providing a closed-loop feedback to the mentor. The visual guidance 170, 172 may be mapped in the remote volume 201 with corresponding parameters such as depth, position, orientation, and velocity in the medical field volume 146. The mapping may include scaling the parameters to generate the visual guidance. The mapping may be adaptively changed as the endoscope 125 is moved or the mentor moves.

At a process 312 the augmented image of the medical field volume may be projected to the operator display device. For example, the augmented stereoscopic image 147 of the medical field volume 146 be projected on the display system 156 of the primary interface system 104 located in an environment 114. The augmented image of the medical field volume thus provides the surgeon S, in the environment 114, instructions and advice for conducting the medical procedure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Further, although the subject matter of some claims may be recited in dependent form from a specific type of claim (e.g., system, apparatus, method, computer readable medium) it is understood that such subject matter may also be claimed as another claim type (e.g., system, apparatus, method, computer readable medium).

Any alterations and further modifications to the described devices, systems, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately.

Various systems and portions of systems have been described in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Although some of the examples described herein refer to surgical procedures or instruments, or medical procedures and medical instruments, the techniques disclosed optionally apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system," are analogous.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A non-transitory machine-readable media storing instructions that, when run by one or more processors, cause the one or more processors to:

generate stereo endoscopic image data of a medical field;

define a medical field volume from the stereo endoscopic image data;

project a three dimensional representation of the medical field volume to an extended-reality display device in a remote volume, the three dimensional representation including a stereoscopic image generated from the stereo endoscopic image data and a three-dimensional scene representing the medical field;

generate visual guidance in the remote volume to augment the stereo endoscopic image, wherein the visual guidance is generated from a user's physical expressions in the remote volume;

map the visual guidance from the remote volume to the medical field volume to generate an augmented image of the medical field volume; and project the augmented image of the medical field volume to a first display device viewed by an operator of one or more instruments in the medical field.

2. The non-transitory machine-readable media of claim 1, wherein the stereo endoscopic image data is generated by an endoscopic imaging device controlled by a robot-assisted manipulator.

3. The non-transitory machine-readable media of claim 2, wherein the medical field includes tools controlled by the robot-assisted manipulator.

4. The non-transitory machine-readable media of claim 1, wherein the medical field volume includes patient anatomy and instruments visible stereo endoscopic image data of the medical field.

5. The non-transitory machine-readable media of claim 1, wherein the medical field volume includes user interface elements.

6. The non-transitory machine-readable media of claim 1 storing instructions that, when run by one or more processors, further cause the one or more processors to receive audio input from an operator at an operator console.

7. The non-transitory machine-readable media of claim 1, wherein the three-dimensional scene is generated by determining an object depth for an object in the stereoscopic image.

8. The non-transitory machine-readable media of claim 1, wherein the three-dimensional scene is generated for a portion of the stereoscopic image.

9. The non-transitory machine-readable media of claim 1, wherein the remote volume moves with extended-reality display device.

10. The non-transitory machine-readable media of claim 1 storing instructions that, when run by one or more processors, further cause the one or more processors to, receive sensor information from the extended-reality display device, wherein the sensor information tracks the user's physical expressions in the remote volume.

11. The non-transitory machine-readable media of claim 1, wherein the user's physical expressions in the remote volume include at least one of freehand gestures, eye gaze, or head motion of a user in the remote volume.

12. The non-transitory machine-readable media of claim 1, wherein the visual guidance includes at least one of include an arrow, a pointer, a ghost hand, a ghost tool, a gaze marker, a virtual anatomical model, or annotations.

13. The non-transitory machine-readable media of claim 1 storing instructions that, when run by one or more processors, further cause the one or more processors to generate audio guidance.

14. The non-transitory machine-readable media of claim 1, wherein mapping the visual guidance includes determining a three-dimensional position for the visual guidance in the medical field volume.

15. The non-transitory machine-readable media of claim 1, wherein mapping the visual guidance includes scaling a parameter from the remote volume to the medical field volume.

16. The non-transitory machine-readable media of claim 1 storing instructions that, when run by one or more processors, further cause the one or more processors to adaptively change the mapping as an endoscopic imaging system moves.

17. The non-transitory machine-readable media of claim 1 storing instructions that, when run by one or more processors, further cause the one or more processors to project a model of a manipulator assembly from the extended-reality display device.

18. The non-transitory machine-readable media of claim 17 storing instructions that, when run by one or more processors, further cause the one or more processors to fuse the model of the manipulator assembly with the augmented image of the medical field volume for display on the extended-reality display device.

19. The non-transitory machine-readable media of claim 1 storing instructions that, when run by one or more processors, further cause the one or more processors to project a model of an operator console from the extended-reality display device.

20. The non-transitory machine-readable media of claim 1, wherein the medical field volume may be a mosaic comprised of a plurality of images and the visual guidance may be visible in an area of the medical field volume visible by moving an endoscopic imaging instrument.

* * * * *